United States Patent
Dubuffet et al.

(10) Patent No.: US 7,179,833 B2
(45) Date of Patent: Feb. 20, 2007

(54) METHOD OF SYNTHESISING PERINDOPRIL AND THE PHARMACEUTICALLY ACCEPTABLE SALTS THEREOF

(75) Inventors: Thierry Dubuffet, Autretot (FR); Jean-Pierre Lecouve, Le Havre (FR)

(73) Assignee: Les Laboratoires Servier, Courbevoie Cedex (FR)

( * ) Notice: Subject to any disclaimer, the term of this patent is extended or adjusted under 35 U.S.C. 154(b) by 0 days.

(21) Appl. No.: 10/562,490

(22) PCT Filed: Jun. 28, 2004

(86) PCT No.: PCT/FR2004/001637

§ 371 (c)(1),
(2), (4) Date: Dec. 22, 2005

(87) PCT Pub. No.: WO2005/003153

PCT Pub. Date: Jan. 13, 2005

(65) Prior Publication Data

US 2006/0178421 A1 Aug. 10, 2006

(30) Foreign Application Priority Data

Jun. 30, 2003 (EP) .................. 03291601

(51) Int. Cl.
*A61K 31/403* (2006.01)
*C07D 209/12* (2006.01)

(52) U.S. Cl. ..................... 514/412; 548/452
(58) Field of Classification Search ............. 514/412; 548/452

See application file for complete search history.

(56) References Cited

U.S. PATENT DOCUMENTS

2005/0171165 A1 * 8/2005 Bhirud et al. ............... 514/360

FOREIGN PATENT DOCUMENTS

| EP | 49658 A1 * | 4/1982 |
| EP | 1321471 | 6/2003 |
| WO | 9633984 | 10/1996 |

OTHER PUBLICATIONS

International Search Report; PCT/FR2004/001637 Nov. 8, 2004.
International Preliminary Examination Report for PCT FR2004 001637, May 11, 2006.

* cited by examiner

*Primary Examiner*—Kamal A. Saeed
*Assistant Examiner*—Michael P. Barker
(74) *Attorney, Agent, or Firm*—Hueschen and Sage

(57) ABSTRACT

Process for the synthesis of perindopril of formula (I):

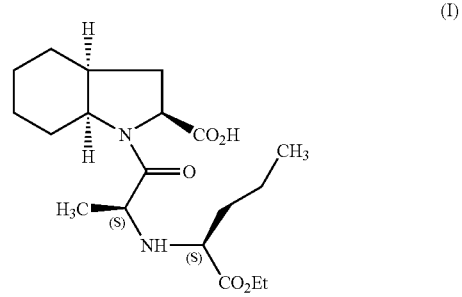

and its pharmaceutically acceptable salts.

4 Claims, No Drawings

METHOD OF SYNTHESISING PERINDOPRIL AND THE PHARMACEUTICALLY ACCEPTABLE SALTS THEREOF

The present invention relates to a process for the synthesis of perindopril of formula (I):

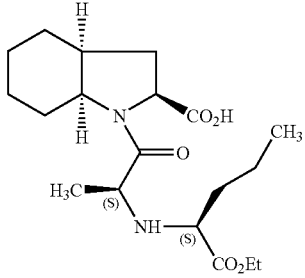

(I)

and its pharmaceutically acceptable salts.

Perindopril and its pharmaceutically acceptable salts, and more especially its tert-butylamine salt, have valuable pharmacological properties.

Their principal property is that of inhibiting angiotensin I converting enzyme (or kininase II), which allows, on the one hand, prevention of the conversion of the decapeptide angiotensin I to the octapeptide angiotensin II (a vasoconstrictor) and, on the other hand, prevention of the degradation of bradykinin (a vasodilator) to an inactive peptide.

Those two actions contribute to the beneficial effects of perindopril in cardiovascular diseases, more especially in arterial hypertension and heart failure.

Perindopril, its preparation and its use in therapeutics have been described in European patent specification EP 0 049 658.

In view of the pharmaceutical value of this compound, it has been important to be able to obtain it by an effective synthesis process, readily transposable to an industrial scale, that leads to perindopril in a good yield and with excellent purity starting from reasonably priced starting materials.

Patent specification EP 0 308 341 describes the synthesis of perindopril by the peptide-type coupling of (2S,3aS,7aS)-octahydroindole-2-carboxylic acid benzyl ester with N-[(S)-1-carboxybutyl]-(S)-alanine ethyl ester, followed by deprotection of the carboxylic group of the heterocycle by catalytic hydrogenation.

That process has the advantage of yielding perindopril in a good yield from starting materials for which industrial synthesis has already been described.

However, it also has drawbacks associated with the use of dicyclohexylcarbodiimide in the coupling step: the formation of coupling impurities, and of dicyclohexylurea, a by-product which is difficult to remove.

The Applicant has now developed a new process for the synthesis of perindopril that avoids the formation of those secondary products.

More specifically, the present invention relates to a process for the synthesis of perindopril and its pharmaceutically acceptable salts which is characterised in that the compound of formula (II):

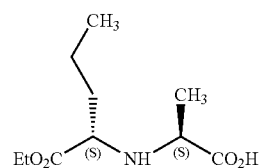

(II)

is reacted with a compound of formula (III):

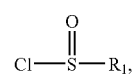

(III)

wherein $R_1$ represents an imidazolyl, benzimidazolyl or tetrazolyl group, to yield the compound of formula (IV):

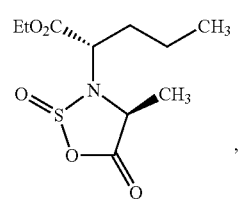

(IV)

which is reacted with a compound of formula (V):

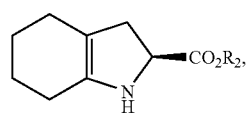

(V)

wherein $R_2$ represents a hydrogen atom, or a benzyl or linear or branched $(C_1-C_6)$alkyl group, or an addition salt thereof with a mineral or organic acid, to yield, after isolation, a compound of formula (VI):

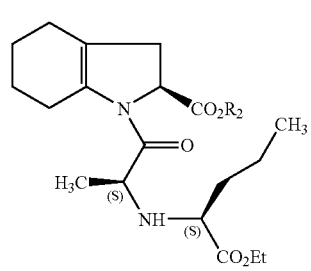

(VI)

wherein $R_2$ is as defined hereinbefore, which is hydrogenated in the presence of a catalyst such as, for example, palladium, platinum, rhodium or nickel, under a hydrogen pressure of from 1 to 30 bars, preferably from 1 to 10 bars, to yield, after deprotection of the acid function where necessary, perindopril of formula (I), which is converted, if desired, into a pharmaceutically acceptable salt, such as the tert-butylamine salt.

The Example hereinbelow illustrates the invention.

EXAMPLE (2S,3aS,7aS)-1-{(2S)-2-[(1S)-1-(ethoxycarbonyl) butylamino]-propionyl}octahydro-1H-indole-2-carboxylic acid tert-butylamine salt Step A: Ethyl(2S)-2-[(4S)-4-methyl-2-oxido-5-oxo-1,2,3-oxathiazolidin-3-yl]-pentanoate Introduce into a reactor 200 g of N-[(S)-ethoxycarbonyl-1-butyl]-(S)-alanine and 1.5 liters of dichloromethane and then, at 0° C., add 325 g of 1H-imidazole-1-sulphinyl chloride. Subsequently, bring the reaction mixture to ambient temperature and then, after stirring for 1 hour, filter off the precipitate formed. The filtrate obtained is evaporated to dryness to yield the expected product in the form of an oil.

Step B: (2S)-1-{(2S)-2-[(1S)-1-(Ethoxycarbonyl) butylamino]propionyl}-2,3,4,5,6,7-hexahydro-1H-indole-2-carboxylic acid Introduce 200 g of (2S)-2,3,4,5,6,7-hexahydro-1H-indole-2-carboxylic acid and 1.5 liters of dichloromethane into a reactor followed by 180 ml of triethylamine.

Subsequently, slowly add a solution of 315 g of the compound obtained in the above Step in 500 ml of dichloromethane and then stir for a further 1 hour at ambient temperature. After the addition of water, the reaction mixture is cooled to 15° C. and the pH is adjusted to 4.2 by the addition of a 2N hydrochloric acid solution. Following extraction, the organic phases are washed and then evaporated to yield the expected product.

Step C: (2S,3aS,7aS)-1-{(2S)-2-[(1S)-1-(ethoxycarbonyl)butylamino]propionyl}-octahydro-1H-indole-2-carboxylic acid Introduce into a hydrogenation vessel 200 g of the compound obtained in the above Step in solution in acetic acid, and then 5 g of 10% Pt/C. Hydrogenate under a pressure of 5 bars at ambient temperature until the theoretical amount of hydrogen has been absorbed. Remove the catalyst by filtration, and then cool to from 0 to 5° C. and recover, by means of filtration, the solid obtained. Wash the cake and dry it to constant weight.

Step D: (2S,3aS,7aS)-1-{(2S)-2-[(1S)-1-(Ethoxycarbonyl)butylamino]propionyl}-octahydro-1H-indole-2-carboxylic acid tert-butylamine salt The compound obtained in the above Step (200 g) is dissolved in 2.8 liters of ethyl acetate, and then 40 g of tert-butylamine and 0.4 liter of ethyl acetate are added.

The suspension obtained is then refluxed until complete dissolution occurs, and the solution obtained is then filtered in the heated state and cooled, with stirring, to a temperature of from 15 to 20° C.

The precipitate obtained is subsequently filtered off, made into a paste again with ethyl acetate, dried and then crushed to yield the expected product in a yield of 95%.

The invention claimed is:

1. A process for the synthesis of perindopril of formula (I):

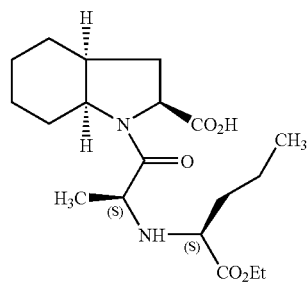

and pharmaceutically acceptable salts thereof,
wherein a compound of formula (II):

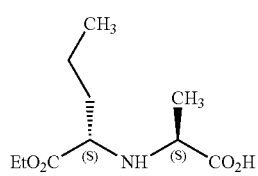

is reacted with a compound of formula (III):

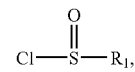

wherein $R_1$ represents imidazolyl, benzimidazolyl or tetrazolyl, to yield a compound of formula (IV):

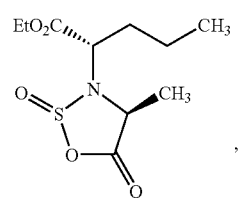

which is reacted with a compound of formula (V):

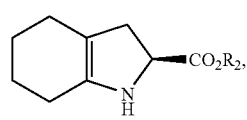

wherein $R_2$ represents hydrogen, benzyl or linear or branched ($C_1$–$C_6$)alkyl, or an addition salt thereof with a mineral or organic acid, to yield, after isolation, a compound of formula (VI):

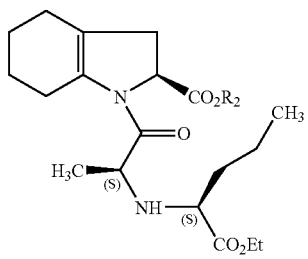 (VI)

which is hydrogenated in the presence of a catalyst, under a hydrogen pressure of from 1 to 30 bars, to yield, after deprotection of the acid function where necessary, perindopril of formula (I), which is converted, if desired, into a pharmaceutically acceptable salt.

2. The process of claim 1, wherein the hydrogen pressure in the hydrogenation reaction is from 1 to 10 bars.

3. The process of claim 1, wherein the catalyst is selected from palladium, platinum, rhodium and nickel.

4. The process of claim 1 for the synthesis of perindopril in the form of its tert-butylamine salt.

* * * * *